US008609404B2

(12) United States Patent
Kapil et al.

(10) Patent No.: US 8,609,404 B2
(45) Date of Patent: Dec. 17, 2013

(54) VACCINES CONTAINING CANINE PARVOVIRUS GENETIC VARIANTS

(75) Inventors: Sanjay Kapil, Stillwater, OK (US); Emily Cooper, Perkins, OK (US)

(73) Assignee: The Board of Regents for Oklahoma State University, Stillwater, OK (US)

( * ) Notice: Subject to any disclaimer, the term of this patent is extended or adjusted under 35 U.S.C. 154(b) by 0 days.

(21) Appl. No.: 13/532,425

(22) Filed: Jun. 25, 2012

(65) Prior Publication Data

US 2012/0263756 A1 Oct. 18, 2012

Related U.S. Application Data

(63) Continuation of application No. 12/211,174, filed on Sep. 16, 2008, now Pat. No. 8,227,583, and a continuation-in-part of application No. 12/138,085, filed on Jun. 12, 2008, now Pat. No. 8,258,274.

(60) Provisional application No. 61/027,618, filed on Feb. 11, 2008, provisional application No. 60/943,947, filed on Jun. 14, 2007.

(51) Int. Cl.
*C12N 15/00* (2006.01)
*C07K 5/00* (2006.01)

(52) U.S. Cl.
USPC ....................... 435/320.1; 536/23.1; 435/69.1

(58) Field of Classification Search
None
See application file for complete search history.

(56) References Cited

U.S. PATENT DOCUMENTS

| | | | | |
|---|---|---|---|---|
| 4,193,990 | A | 3/1980 | Appel et al. | |
| 4,193,991 | A | 3/1980 | Appel et al. | |
| 4,303,645 | A | 12/1981 | Carmichael et al. | |
| 4,971,793 | A | 11/1990 | Wood et al. | |
| 5,077,195 | A | 12/1991 | Blalock et al. | |
| 5,449,608 | A | 9/1995 | Young et al. | |
| 5,814,510 | A | 9/1998 | Parrish et al. | |
| 5,882,652 | A | 3/1999 | Valdes et al. | |
| 5,885,585 | A | 3/1999 | Parrish et al. | |
| 5,905,040 | A | 5/1999 | Mazzara et al. | |
| 6,187,759 | B1 | 2/2001 | Tarpey et al. | |
| 6,936,442 | B2 | 8/2005 | Pichuantes et al. | |
| 7,445,889 | B2 | 11/2008 | Smith-Norowitz et al. | |
| 8,227,583 | B2 * | 7/2012 | Kapil et al. ................. | 536/23.1 |
| 2006/0008469 | A1 | 1/2006 | Brown et al. | |

FOREIGN PATENT DOCUMENTS

| | | | |
|---|---|---|---|
| WO | 96/14088 | A1 | 5/1996 |
| WO | 02/00883 | A2 | 1/2002 |
| WO | 2008/032796 | A1 | 3/2008 |
| WO | PCT/US08/66720 | | 6/2008 |
| WO | PCT/US09/056930 | | 9/2009 |

OTHER PUBLICATIONS

Lopez et al. (Journal of Medicine, 1992, vol. 66, p. 2748-2753).*

AAHA, "2006 AAHA Canine Vaccine Guidelines", 2005, pp. 1-28, Publisher: American Animal Hospital Association, Published in: US.

Alexandrov et al., "Fluorescent and electron-microscopy immunoassays employing polyclonal and monoclonal antibodies for detection of goose parvovirus infection", "Journal of Virological Methods 79", 1999, pp. 21-32.

Michael C. Angellotti, "CodonO: codon usage bias analysis within and across genomes", May 1, 2007, vol. 35, Publisher: Nucleic Acids Research, Published in: US.

Buonavoglia, et al. , "Evidence for evolution of canine parvovirus type 2 in Italy", "Journal of General Virology", 2001, pp. 3021-3025, vol. 82, Published in: GB.

Coleman, Robert et al., "Virus Attenuation by Genome-Scale Changes in Codon Pair Bias ", "Science", Jun. 27, 2008, pp. 1784-1787, vol. 320, Publisher: AAAS, Published in: US.

Decaro, et al. , "Tissue distribution of the antigenic variants of canine parvovirus type 2 in dogs", "Science Direct—Veterinary Microbiology", 2007, pp. 39-44, vol. 121, Publisher: Elsevier, Published in: US.

Desario, et al. , "Canine parvovirus infection: Which diagnostic test for virus?", "Journal of Virological Methods", Feb. 6, 2005, pp. 179-185, vol. 126, No. 1-2, Publisher: Elsevier, Published in: US.

Dorsman et al., "Strong aggregation and increased toxicity of polyleucine over polyglutamine stretches in mammalian cells", 2002, pp. 1487-1496, vol. II, No. 13, Publisher: Human Molecular Genetics.

Enserink, Martin, "'Biased' Viruses Suggest New Vaccine Strategy for Polio and Other Diseases", "Science", Jun. 27, 2008, p. 1709, vol. 320, Publisher: AAAS, Published in: US.

Feng, "Construction and immune potency of recombinant adenovirus containing codon-modified HIV-1 gp120", "PubMed", Jun. 2004, pp. 113-117, vol. 18, No. 2, Publisher: NCBI, Published in: US.

Fuglsang, Anders, "The effective number of codons for individual amino acids: some codons are more optimal than others ", "Gene", Jul. 22, 2003, pp. 185-190, vol. 320, Publisher: Elsevier, Published in: US.

Garg, Himanshu, et al., "Single amino acid change in gp41 region of HIV-1 alters bystander apoptosis and CD4 decline in humanized mice", 2011, Publisher: Virology Journal, Published in: US.

"The Genetic Code", "Biology Pages", Apr. 22, 2010, Published in: US.

Greene, "Infectious Diseases of the Dog and Cat, 3rd ed.", Article pertaining to vaccination recommendations, "Canine Veterinary Journal 2007", 2006, pp. 69, 1105-1108, vol. 3, Publisher: Elsevier, Published in: Canada.

Grant Rezabek, et al. , "Doc It Can't be Parvo My Dog is Vaccinated!!", "Oklahoma Animal Healthy Update, Fall 2006", Aug. 30, 2006, pp. 4-5, Publisher: Oklahoma State University, Veterinary Health Sciences, Published in US.

Inomata, et al., "A single-amino-acid change of the gustatory receptor gene Gr5a, has a major effect on Trehalose Sensitivity in a natural", Aug. 2004, pp. 1749-1758, vol. 167, Publisher: Genetics Sociery of America, Published in: US.

(Continued)

*Primary Examiner* — Agnieszka Boesen

(74) *Attorney, Agent, or Firm* — Fellers, Snider, Blankenship, Bailey & Tippens, P.C.

(57) ABSTRACT

Canine parvovirus vaccines and diagnostics and methods for their use are provided. The vaccines are effective against emerging canine parvovirus variants.

17 Claims, 9 Drawing Sheets

(56) References Cited

OTHER PUBLICATIONS

Malik, Tahir, et al., "Single Amino acid changes in the mumps virus maemagglutinin-neurainidase and polymerase proteins are associated with neu", pp. 1741-1747, vol. 90, Publisher: Journal of Genetic Virology, Published in: Great Britain.

McKenna, et al., "Three-Dimensional Structure of Aleutian Mink Disease Parvovirus: Implications for Disease Pathogenicity", "Journal of Virology", Aug. 1999, pp. 6882-6891, vol. 73, No. 8, Publisher: American Society for Microbiology, Published in: US.

Nakamura, et al., "Pathogenic Potential of Canine Parvovirus Types 2a and 2c in Domestic Cats", "Clinical and Diagnostic Laboratory Immunology", May 2001, pp. 663-668, vol. 8, No. 3, Publisher: American Society for Microbiology, Published in: US.

Nakamura, et al., "A novel antigenic variant of Canine parvovirus from a Vietnamese dog.", "PubMed", Jul. 15, 2004, pp. 2261-2269, vol. 149, No. 11, Publisher: Arch Virology, Published in: US.

Nellist, Mark, et al., "Distinct Effects of Single Amino-Acid Changes to Tuberin on the Function of the Tuberin-Hamartin Complex", 2005, pp. 59-68, No. 13, Publisher: European Journal of Human Genetics, Published in: Europe.

"Oklahoma Animal Disease Diagnostic Laboratory Hot Topics", "Animal Health Update—Winter 2006", Publisher: Oklahoma State University, Veterinary Health Sciences, Published in: US.

Parrish, et al., "The Origins of New Pandemic Viruses: The Acquisition of New Host Ranges by Canine Parvovirus and Influenza A Viruses", "The Annual Review of Microbiology", 2005, pp. 553-586, vol. 59, Publisher: Annual Reviews, Published in: US.

Pereira, et al., "Selective regimen shift and demographic growth increase associated with the emergency of high-fitness variants of canine", "Science Direct", Mar. 7, 2006, pp. 1-11, vol. 263, Publisher: Elsevier, Published in: Brazil.

Kapil, Sanjay et al., "Slide set, Canine Parvovirus Variants Circulating in South-Central USA", presented at Western Veterinary Conference, Feb. 2007, Published in: US.

Truyen, "Evolution of canine parvovirus—A need for new vaccines?", "Canine and Feline Vaccination", Apr. 18, 2006, pp. 9-13, vol. 117, No. 1, Publisher: Veterinary Microbiology, Published in: US.

Vicario, Saverio, "Codon usage in twelve species of *Drosophila*", "BMC Evolutionary Biology", Nov. 15, 2007, vol. 7, No. 226, Publisher: BioMed Central, Published in: US.

"Codon usage bias", Nov. 4, 2011, Publisher: Wikipedia, Published in: US.

Wong, Emily HM, "Codon usage bias and the evolution of influenza A viruses. Codon Usage Biases of Influenza Virus", "BMC Evolutionary Biology", 2010, vol. 10, No. 253, Publisher: BioMed Central, Published in: US.

Ning Zhi, "Codon Optimization of Human Parvovirus B19 Capsid Genes Greatly Increases Their Expression in Nonpermissive Cells", "Journal of Virology", Dec. 31, 2010, pp. 13059-13062, vol. 84, No. 24, Publisher: American Society for Microbiology, Published in: US.
Perez, et al., "First Detection of Canine Parvovirus Type 2c in South America", 2007, pp. 147-152, vol. 124, Publisher: Veterinary Microbiology, Published in: US.
Sassa, et al., "Neutralizing Antibodies Against Feline Parvoviruses in Nondomestic Felids Inoculated With Commercial Inactivated . . . ", 2006, pp. 1195-1198, vol. 68, No. 11, Publisher: Journal of Veterminary Medicine, Published in: US.
Japan Patent Application No. 2010-512351 Office Action, dispatched Feb. 20, 2013, in Japanese with English translation.
Pakula, Andrew et al., "Genetic Analysis of Protein Stability and Function", 1989, pp. 289-310, vol. 23, Publisher: Ann. Rev. Genet., Published in: US.
Soares, Rodrigo, et al., "Genetic Variability of Porcine Parvovirus Isolates Revealed by Analysis of Partial Sequences of the Structural Coding Gene VP2", 2003, pp. 1505-1515, vol. 84, Publisher: Journal of General Virology, Published in: US.

* cited by examiner

426
GATGATAATGTATTGCTACCAACAGATCCAATTGGAGGTAAAACAGGAATTAACTA

TACTAATATATTTAATACTTATGGTCCTTTAACTGCATTAAATAATGTACCACCAGTT

TATCCAAATGGTCAAATTTGGGATAAAGAATTTGATACTGACTTAAAACCAAGACTT
494
CATGTAAATGCACCATTTGTTTGTCAAAATAATTGCCCTGGTCAATTATTTGTAAAA

GTTGCGCCTAATTTAACAAATGAATATGATCCTGATGCATCTGCTAATATGTCAAGA

ATTGTAACTTACTCAGATTTTTGGTGGAAAGGTAAATTAGTATTTAAAGCTAAACTA

AGAGCCTCTCATACTTGGAATCCAATTCAACAAATGAGTATTAATGTAGATAACCAA
572
TTTAACTATGTACCAAGTAATATTGGAGGTATGAAAATTGTCTATGAAAAATCTCAA

CTAGCACCTAGAAAATTATATTAACATACTTACTATGTTTTATGTTTATTACATAT

Figure 1

426          431
GATGATAATGTATTG<u>CTG</u>CCAACAGATCCAATTGGAGGTAAAACAGGAATTAACTA

TACTAATATATTTAATACTTATGGTCCTTTAACTGCATTAAATAATGTACCACCAGTT

TATCCAAATGGTCAAATTTGGGATAAAGAATTTGATACTGACTTAAAACCAAGACTT
                                494
CATGTAAATGCACCATTTGTTTGTCAAAATAAT<u>TGC</u>CCTGGTCAATTATTTGTAAAA

GTTGCGCCTAATTTAACAAATGAATATGATCCTGATGCATCTGCTAATATGTCAAGA

ATTGTAACTTACTCAGATTTTGGTGGAAAGGTAAATTAGTATTTAAAGCTAAACTA

AGAGCCTCTCATACTTGGAATCCAATTCAACAAATGAGTATTAATGTAGATAACCAA
                            572
TTTAACTATGTACCAAGTAATATTGGAGGTATGAAAATT<u>GTC</u>TATGAAAAATCTCAA

CTAGCACCTAGAAAATTATATTAACATACTTACTATGTTTTATGTTTATTACATAT

Figure 2

426
GAAGATAATGTATTGCTACCAACAGATCCAATTGGAGGTAAAACAGGAATTAACTA

TACTAATATATTTAATACTTATGGTCCTTTAACTGCATTAAATAATGTACCACCAGTT

TATCCAAATGGTCAAATTTGGGATAAGAATTTGATACTGACTTAAAACCAAGACTT
                                                494
CATGTAAATGCACCATTTGTTTGTCAAAATAATTGTCCTGGTCAATTATTTGTAAAA

GTTGCGCCTAATTTAACAAATGAATATGATCCTGATGCATCTGCTAATATGTCAAGA

ATTGTAACTTACTCAGATTTTGGTGGAAAGGTAAATTAGTATTTAAAGCTAAACTA

AGAGCCTCTCATACTTGGAATCCAATTCAACAAATGAGTATTAATGTAGATAACCAA
                                         572
TTTAACTATGTACCAAGTAATATTGGAGGTATGAAAATTGTA

Figure 3

426                                                           440
GAAGATAATGTATTGCTACCAACAGATCCAATTGGAGGTAAAGCAGGAATTAACTA

TACTAATATATTTAATACTTATGGTCCTTTAACTGCATTAAATAATGTACCACCAGTT

TATCCAAATGGTCAAATTTGGGATAAAGAATTTGATACTGACTTAAAACCAAGACTT
                                        494
CATGTAAATGCACCATTTGTTTGTCAAAATAATTGTCCTGGTCAATTATTTGTAAAA

GTTGCGCCTAATTTAACAAATGAATATGATCCTGATGCATCTGCTAATATGTCAAGA

ATTGTAACTTACTCAGATTTTTGGTGGAAAGGTAAATTAGTATTTAAAGCTAAACTA

AGAGCCTCTCATACTTGGAATCCAATTCAACAAATGAGTATTAATGTAGATAACCAA
                                                    572
TTTAACTATGTACCAAGTAATATTGGAGGTATGAAAATTGTA

Figure 4

```
426             430                                          440
GAAGATAATGTATTACTACCAACAGATCCAATTGGAGGTAAAGCAGGAATTAACTA

TACTAATATATTTAATACTTATGGTCCTTTAACTGCATTAAATAATGTACCACCAGTT

TATCCAAATGGTCAAATTTGGGATAAAGAATTTGATACTGACTTAAAACCAAGACTT
                                         494
CATGTAAATGCACCATTTGTTTGTCAAAATAATTGTCCTGGTCAATTATTTGTAAAA

GTTGCGCCTAATTTAACAAATGAATATGATCCTGATGCATCTGCTAATATGTCAAGA

ATTGTAACTTACTCAGATTTTGGTGGAAAGGTAAATTAGTATTTAAAGCTAAACTA

AGAGCCTCTCATACTTGGAATCCAATTCAACAAATGAGTATTAATGTAGATAACCAA
                                                       572
TTTAACTATGTACCAAGTAATATTGGAGGTATGAAAATTGTA
```

Figure 5

426
GAC GATAATGTATTGCTACCAACAGATCCAATTGGAGGTAAAACAGGAATTAACTA

TACTAATATATTTAATACTTATGGTCCTTTAACTGCATTAAATAATGTACCACCAGTT

TATCCAAATGGTCAAATTTGGGATAAAGAATTTGATACTGACTTAAAACCAAGACTT
      484                          494
CATGTGAATGCACCATTTGTTTGTCAAAATAATTGCCCTGGTCAATTATTTGTAAAA

GTTGCGCCTAATTTAACAAATGAATATGATCCTGATGCATCTGCTAATATGTCAAGA

ATTGTAACTTACTCAGATTTTTGGTGGAAAGGTAAATTAGTATTTAAAGCTAAACTA
              546
AGAGCCTCTCATACTTGGAACCCAATTCAACAAATGAGTATTAATGTAGATAACCAA
                       572
TTTAACTATGTACCAAGTAATATTGGAGGTATGAAAATTGTC

Figure 9

VACCINES CONTAINING CANINE PARVOVIRUS GENETIC VARIANTS

CROSS-REFERENCE TO RELATED APPLICATIONS

This application is a continuation of U.S. patent application Ser. No. 12/211,174 filed Sep. 16, 2008, now U.S. Pat. No. 8,227,583 which claims benefit of U.S. provisional patent application 61/027,618, filed Feb. 11, 2008, and is a continuation-in-part of U.S. patent application Ser. No. 12/138,085, filed Jun. 12, 2008, now U.S. Pat. No. 8,258,274 which also claims benefit of U.S. provisional patent application 61/027,618, filed Feb. 11, 2008 and U.S. provisional patent application 60/943,947, filed Jun. 14, 2007, the complete contents of each of which are hereby incorporated by reference.

SEQUENCE LISTING

This application includes as the Sequence Listing the complete contents of the accompanying text file "Sequence.txt", created Aug. 28, 2008, containing 4406 bytes, hereby incorporated by reference.

DESCRIPTION

Background of the Invention

1. Field of the Invention

The invention generally relates to improved canine parvovirus (CPV) vaccine formulations and diagnostic tests. In particular, the invention provides improved CPV vaccine formulations and diagnostic tests comprising newly emerging dominant CPV variants currently circulating in canine populations.

2. Background of the Invention

Canine parvovirus (CPV) is primarily an enteric pathogen that infects dogs, especially young dogs. Parvovirus infection is characterized by acute diarrhea, fever and leukopenia in dogs and puppies more than 4 to 5 weeks old, and myocardial disease in younger puppies. The mortality rate from the disease in unvaccinated dogs is very high. While vaccines against CPV are available, because CPV is a single-stranded DNA virus and has an extreme ability to mutate, the virus shows a remarkable ability to vary antigenically and thereby elude the immune protection afforded by vaccines. Thus, constant monitoring of the antigenic type and genotype of the causative agent is necessary.

CPV was first isolated in 1978 and was named "CPV-2" to distinguish it from parvovirus canine Minute virus (CMV or CPV-1). CPV-2 is generally believed to be a genetic variant of feline panleukopenia virus (FPV) or of the mink enteric virus (MEV), and is genetically and antigenically very closely related to parvoviruses that infect minks, foxes, raccoons, and other carnivores. The CPV capsid contains a single-stranded DNA genome of about 5200 bases with only two open reading frames, although at least four proteins are encoded due to alternative mRNA splicing. Parvovirus capsid is made up of two viral proteins (VP), VP1 and VP2, with VP2 being the major immunogenic parvovirus capsid protein. A genetic variant of the original CPV isolate was identified in 1979-1980 and was named CPV type 2a. In the mid-1980's, yet another variant, type 2b, was identified, and since then, types 2a and 2b appear to have completely displaced the original CPV-2. Current vaccines are directed against only the 2a and 2b variants, yet the 2a variant is no longer detected in the United States. For a review of CPV discovery and evolution, see Parrish and Kawaoka, 2005.

CPV-2b differs from CPV-2a at only two amino acid positions: Asn-426 in 2a (encoded by AAT) is Asp in 2b (encoded by GAT), and Ile-555 in 2a is Val in 2b. The Ile-555 to Val change is actually a reversion to the original type 2 sequence. The CPV-2a and 2b antigenic types appeared to be relatively stable for a number of years. However, in 2000 a variant "2c" was described in which position 426 is Glu encoded by GAA (position 555 remains Val). The 2c variant has been reported in Italy (Buonavoglia et al., 2001), Vietnam (Nakamura et al., 2001) and other countries, including Spain (Nakamura et al., 2004; Decaro et al., 2006), but until now there have been no confirmed reports of the 2c variant in the United States, and CPV vaccines have not been updated to include such variants. This is of special importance because, unlike previously described variants that infect primarily puppies, CPV2c has the ability to infect adult dogs. Further, the sequence of a 2b variant with codon variations at positions 494 and 572 was submitted to GenBank (gi: 54646340) in 2003 and reported by Shackelton et al. in 2005 (*Proceedings National Academy Sciences* 102:379-384), but no alterations in CPV vaccine or diagnostic compositions were proposed based on such sequences. This may be in part due to the nature of the mutations, which are "silent" with respect to the encoded amino acids, i.e. the translated amino acid sequence of 2b and the 2b variant with codon variations at positions 494 and 572 are the same. However, recent studies concerning codon bias (Enserink, 2008. Science 320: 1709; Coleman 2008, Science 320; 1784-87) show that codon bias may be a very important evolutionary tool of organisms. Enserink states that "... many organisms, including viruses, have a bias toward certain codons in their genes. This may be because those codons are easier to translate at ribosomes ... thus speeding up protein production ...". Therefore, to successfully combat diseases for which viruses are the etiological agent, it is advisable to continuously monitor emerging variants and include prevalent variants in new, updated vaccine preparations, even if the changes that are detected do not result in a change in a translated amino acid sequence.

Several problems arise when vaccines are not updated. Firstly, even vaccinated dogs may be susceptible to infection by CPV variants that are not included in the vaccine. Secondly, when vaccinated dogs become ill, their owners frequently claim that the viral strains in the vaccine caused the disease. This has frequently resulted in the payment of remuneration to the owners, since there is no practical way for the vaccine company to provide evidence to the contrary.

Several CPV vaccine preparations have been proposed:

U.S. Pat. Nos. 4,193,990 and 4,193,991 to Appel et al., describe heterotypic and inactivated ("killed") virus vaccines, respectively, in which the exemplary vaccine afforded protection against the original CPV.

U.S. Pat. No. 4,303,645 to Carmichael et al., describes a vaccine comprising an attenuated CPV produced by prolonged serial passage of the virus in non-oncogenic cell lines. The exemplary vaccine also protects against the original CPV isolate.

U.S. Pat. No. 4,971,793 to Wood et al., and U.S. Pat. No. 5,882,652 to Valdes et al., both describe recombinant subunit vaccines comprising the CPV VP-2 protein produced in recombinant baculovirus. The VP-2 protein is of no specified type or subtype.

U.S. Pat. No. 5,885,585 to Parrish et al., describes a CPV vaccine comprising an attenuated form of a 2b variant.

Due to the ability of the CPV virus to mutate and develop new antigenic variants, there is an ongoing need to monitor the genetic makeup of CPV variants and to develop vaccines and diagnostic tests that reflect current CPV variants.

SUMMARY OF THE INVENTION

The present invention provides updated vaccines for preventing CPV infection, and diagnostic methods for detecting new and emerging CPV variants. The vaccines and diagnostic methods are based on the discovery of previously unknown and previously unappreciated CPV variants, and take into account the emergence of mutant forms of the virus for which prior vaccine formulations and diagnostics are inadequate. The vaccines of the present invention provide protection against emerging forms of CPV, and the diagnostics provide the ability to detect the newly evolved forms of the virus, both of which capabilities were previously unavailable. In particular, new rare variants are useful as "marker" variants in vaccines. Use of the marker variant makes possible forensic investigations of whether or not disease symptoms in an animal vaccinated with the marker variant are caused by the vaccine, or by another strain of CPV.

The new vaccine formulations include whole attenuated CPV with single-stranded DNA having one or more of the following characteristics:

2bΔ494Δ572 is a 2b CPV variant which contains at least the following changes: the codon encoding VP2 protein position 494 is TGC rather than TGT, and the codon encoding VP2 protein position 572 is GTC rather than GTA. These changes do not result in amino acid changes (both TGC and TGT encode cysteine and both GTC and GTA encode valine). Nevertheless, this variant causes disease in animals that have been previously vaccinated with conventional, currently available vaccines and should be incorporated into new vaccine formulations. While the changes at positions 494 and 572 were previously described, they were not appreciated. Further, this American isolate may contain other mutations. The sequence of 2b is set forth in SEQ ID NO: 1.

2bΔ431Δ494Δ572 (also referred to herein as "2bΔ431") is a newly discovered rare 2b CPV variant (e.g. a variant of 2bΔ494Δ572) in which the codon encoding position 431 of the VP2 protein is CTG rather than CTA. While this change also does not result in an amino acid change, this variant nevertheless also causes disease in vaccinated animals and may be incorporated into new vaccine formulations. Significantly, due to its scarcity, 2bΔ431 represents an ideal vaccine "marker" sequence. The sequence of 2bΔ431 is set forth in SEQ ID NO: 2.

2bΔ426Δ484Δ494Δ546Δ572 (also referred to herein as "2bΔ426Δ484Δ546") is a newly discovered 2b CPV variant (i.e. a variant of 2bΔ494Δ572) which contains the same changes as 2bΔ494Δ572 and, in addition, has changes at positions 426, 484 and 546. Position 426 is encoded by GAC (instead of GAT), position 484 is encoded by GTG (instead of GTA) and position 546 is encoded by AAC (instead of AAT). These changes do not result in amino acid changes (both GAC and GAT encode asparagine, both GTG and GTA encode valine, and both AAC and AAT encode asparagine. Nevertheless, this new variant, which was isolated from animals that have been previously vaccinated with conventional, currently available vaccines, is very cytopathic and should be incorporated into new vaccine formulations, and may be utilized as a marker vaccine as described below. The sequence of 2bΔ426Δ484Δ546 is set forth in SEQ ID NO: 6.

American (or United States) 2c is the first 2c variant isolated in the United States and is the predominant (81%) 2c variant. This variant is also referred to as the "major 2c variant" or as "major American 2c". The sequence of this variant is set forth in SEQ ID NO: 3.

2cΔ440 (also referred to herein as is a newly discovered 2c CPV variant in which the codon encoding position 440 of the VP2 protein is GCA, rather than ACA, which results in a change in the amino acid sequence from threonine (ACA) to alanine (GCA) at this position. This variant causes disease in vaccinated animals and should be incorporated into new vaccine formulations. This variant is currently a minor (19%) variant and is also referred to herein as the "minor 2c variant" or as "Minor American 2c". The sequence of this variant is set forth in SEQ ID NO: 4.

2cΔ430Δ440, a further variant of 2cΔ440, which, in addition to containing GCA at the codon for position 440, also varies from known 2c sequences by having the leucine at position 430 encoded by TTA rather than the usual TTG. The sequence of 2cΔ430Δ440 is set forth in SEQ ID NO: 5.

All of these CPV variants were detected by polymerase chain reaction (PCR) and isolated in cell culture from CPV infected dogs and/or their puppies that had already been vaccinated against CPV using conventional commercial vaccines. Thus, these newly emerging variants are capable of escaping immune surveillance in dogs vaccinated according to current protocols, whether the variation does (e.g. 2cΔ440 and 2cΔ430Δ440 in part) or does not (e.g. 2bΔ494Δ572, 2bΔ431, 2bΔ426Δ484Δ546) change in the amino acid sequence of the VP2 protein at the indicated positions. In addition, currently available diagnostic techniques for field use do not detect the new CPV variants or react poorly, leading to decreased sensitivity. The present invention solves these problems by providing vaccines and diagnostics that take the new variants into account.

The invention further provides a method of propagating canine parvovirus, particularly the variants described herein, which do not produce a cytopathic affect (CPE) or produce only a mild CPE, when cultured in CRFK cells alone. The method comprises the step of culturing the canine parvovirus in a mixture of Crandall Reese feline kidney (CRFK) cells and Vero cells in a suitable medium. The step of culturing is carried out under conditions that allow the canine parvovirus to propagate to titers higher than those attained when the CPV is cultured in CRFK cells alone.

The invention further provides a parvovirus vaccine comprising one or more CPV variants. The level of neutralization of the one or more CPV variants is at least 4-fold lower than the level of neutralization of one or more CPV variants selected from the group consisting of CPV-2, CPV-2a, CPV-2b and CPV-2c, as determined using serum from an animal vaccinated with a vaccine comprising one or more of CPV variants CPV-2, CPV-2a, CPV-2b and CPV-2c. In some embodiments, the levels of neutralization are determined by a serum neutralization assay and expressed as a neutralization titer.

BRIEF DESCRIPTION OF THE DRAWINGS

FIG. 1. Exemplary 2bΔ494Δ572 sequence (the nucleic acid sequence set forth in SEQ ID NO: 1) in which the codon for position 494 is TGC and the codon for position 572 is GTC. The nucleic acid sequence encoding amino acids 426 to 572 of the VP2 protein is shown.

FIG. 2. An exemplary 2bΔ431 sequence (the nucleic acid sequence set forth in SEQ ID NO: 2) in which the codon for position 431 is CTG. The nucleic acid sequence encoding amino acids 426 to 572 of the VP2 protein is shown.

FIG. 3. The nucleic acid sequence encoding amino acids 426 to 572 (the nucleic acid sequence set forth in SEQ ID NO: 3) of the major American 2c VP2 protein is shown.

FIG. 4. An exemplary 2cΔ440 (minor American 2c) sequence (the nucleic acid sequence set forth in SEQ ID NO: 4) in which the codon for position 440 is GCA instead of ACA, encoding alanine instead of threonine. The nucleic acid sequence encoding amino acids 426 to 572 of the VP2 protein is shown.

FIG. 5. An exemplary 2cΔ430Δ440 sequence (the nucleic acid sequence set forth in SEQ ID NO: 5).

FIG. 9. An exemplary 2bΔ426Δ484Δ494Δ546Δ572 sequence (the nucleic acid sequence set forth in SEQ ID NO: 6).

DETAILED DESCRIPTION OF THE PREFERRED EMBODIMENTS OF THE INVENTION

Figure 6:
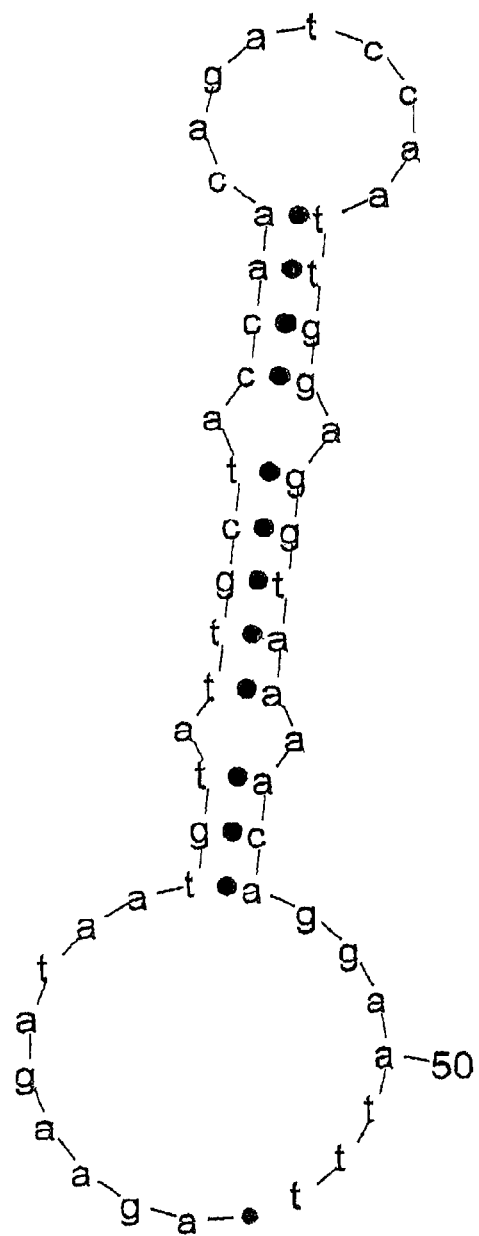
FIG. 6. Putative folded structure associated with the 2c variant.

The present invention provides CPV vaccines and diagnostics, the compositions of which include newly discovered variants that reflect the evolutionary trends of CPV. Each of the variants was isolated from a dog that had already been vaccinated for CPV, but which nevertheless contracted CPV and became ill. Thus, in order to stop or curtail the spread of CPV, these new variants may be incorporated into vaccine protocols. Further, as described in detail below, the identification of these variants has led to the discovery of a hypervariable region in the CPV genome.

The discovery of the variants described herein has led to the identification of a crucial hypervariable (HPV) region of the CPV genome. In the past, only nucleotides at positions 1276 to 1277 have been considered important. However, the epidemiological discoveries described herein have shown that the critical HPV region actually falls almost in the middle of the CPV genome from position 1275-1326 of the complete VP2 gene. This HPV region encompasses at least two critical hypervariable codons, codons 426 and 440 of the VP2 gene. Preferably, the hypervariable region comprises the region beginning one nucleotide before codon 426 through codon 440. Without being bound by theory, it is likely that the biological significance of this HPV region is related to the thermodynamic stability of the structures that are formed by the sequence, as discussed more fully below.

The six variants are as follows:

1) 2bΔ494Δ572 is a 2b CPV variant in which the codon for position 494 of the VP2 protein is TGC rather than TGT and the codon for position 572 of the VP2 protein is GTC rather than GTA. Neither of these mutations causes a change in the encoded amino acids (Cys at position 494 and Val at position 572) and these sequences have previously been described. Nevertheless, it was not previously appreciated that these changes allow the virus to evade immune clearance in hosts vaccinated with currently available vaccines, as described herein. This variant is depicted in FIG. 1, where a portion of a 2b (i.e. 426=GAT) VP2 gene encoding amino acids 426 to 572 is shown. The two mutant codons (494 and 572) are shown in bold and underlined.

2) 2bΔ431 is a rare 2b CPV variant in which contains a change from CTA to CTG at the codon encoding position 431. The original 2bΔ431 isolate also included the 2bΔ494Δ572 mutations and is hence 2bΔ431Δ494Δ572. However, the invention encompasses any CPV sequence (2a, 2b or 2c) that includes CTG at the codon encoding position 431 of the VP2 protein. This mutation does not result in an amino acid change (CTA and CTG both encode Leu) but, due to its scarcity, 2bΔ43) represents an ideal vaccine "marker" sequence for forensic purposes. This aspect of the invention is discussed in detail below. This variant is depicted in FIG. 2, where a portion of a 2b (i.e. 426=GAT) VP2 gene encoding amino acids 426 to 572 is shown. The three mutant codons (431, 494 and 572) are shown in bold and underlined.

3) American 2c is the first 2c variant isolated in the United States. The significant emergence of this variant was previously unappreciated (see FIG. 3).

4) 2cΔ440 is a 2c CPV variant in which the codon for position 440 of the VP2 protein is GCA, rather than ACA. This mutation results in an amino acid change from Thr to Ala at position 440. Further, this mutant was also isolated from a previously vaccinated dog that nevertheless fell ill with CPV. Therefore, this variant sequence should be incorporated into new CPV vaccine and diagnostic preparations. This variant is depicted in FIG. 4, where a portion of a 2c VP2 gene (i.e. 426=GAA) encoding amino acids 426 to 572 is shown. The mutant codon (440) is shown in bold and underlined. Codons 494 and 572 are underlined for reference.

5) 2cΔ430Δ440, a further variant of 2cΔ440, which, in addition to containing GCA at the codon for position 440, also varies from known 2c sequences by having the leucine at position 430 encoded by TTA rather than the usual TTG. This variant is depicted in FIG. 5.

6) 2bΔ426Δ484Δ494Δ546Δ572 is a variant of 2bΔ494Δ572 which contains further changes at positions 426, 484 and 546. Position 426 is encoded by GAC instead of GAT, position 484 is encoded by GTG (instead of GTA) and position 546 is encoded by AAC (instead of AAT). While these changes do not result in amino acid changes (position 426 is asparagine, position 484 is valine and position 546 is asparagine in the variants, this new variant is extremely cytopathic and should be incorporated into new vaccine formulations. While this isolate has the same amino acid sequence as CPV-2b, the codon GAC at position 426 is extremely rare, and this isolate can also be used as a forensic marker vaccine, as described below.

Table 1 provides a summary of the sequence changes in these variants.

TABLE 1

Codons associated with critical amino acids of the VP2 protein in current United States CPV variants

| Variant and SEQ ID NO: | Amino acid position and associated codon | | | | | | | |
|---|---|---|---|---|---|---|---|---|
| | 426 | 430 | 431 | 440 | 484 | 494 | 546 | 572 |
| 2bΔ494Δ572 SEQ ID NO: 1 | GAT | TTG | CTA | ACA | GTA | TGC* | AAT | GTC* |

TABLE 1-continued

Codons associated with critical amino acids of the VP2 protein in current United States CPV variants

| Variant and SEQ ID NO: | Amino acid position and associated codon | | | | | | | |
|---|---|---|---|---|---|---|---|---|
| | 426 | 430 | 431 | 440 | 484 | 494 | 546 | 572 |
| 2bΔ431Δ494Δ572 ("2bΔ431") SEQ ID NO: 2 | GAT | TTG | CTG* | ACA | GTA | TGC* | AAT | GTC* |
| 2bΔ426Δ484Δ494Δ546Δ572 ("2bΔ426Δ484Δ546") SEQ ID NO: 6 | GAC* | TTG | CTA | ACA | GTG* | TGC* | AAC* | GTC* |
| American 2c ("Major American 2c") SEQ ID NO: 3 | GAA | TTG | CAT | ACA | GTA | TGT | AAT | GTA |
| 2cΔ440 ("Minor American 2c") SEQ ID NO: 4 | GAA | TTG | CAT | GCA* | GTA | TGT | AAT | GTA |
| 2cΔ430Δ440 SEQ ID NO: 5 | GAA | TTA* | CAT | GCA* | GTA | TGT | AAT | GTA |

*indicates a mutant codon

While the changes at positions 494 and 572 were previously described, the emerging predominance and characteristics of this variant were previously unappreciated. All variants described herein were isolated from dogs (or their offspring) that had already been vaccinated against CPV but which became ill and died from CPV. Although the variants were first identified in the south-central United States, they are believed to be responsible for sporadic reports of vaccine-resistant parvovirus illness in dogs in other parts of the US as well. Variant 2c previously detected in all continents except Australia and Africa, has now been detected in 14 states (Alabama, Arizona, Arkansas, California, Delaware, Florida, Illinois, Kansas, Jew Jersey, Missouri, Oregon, Oklahoma, South Carolina, and Texas). Given the history of rapid dissemination of previously known CPV variants, one or more of these variants should immediately be included in vaccines throughout the world in order to halt the spread of these most recent iterations of the virus. Further, CPV diagnostic tests and methods should be reformulated to take these emerging variants into account.

As described in the Examples section, the onset of disease symptoms and death in the vaccinated dogs from which the CPV variants of the invention were isolated was extremely rapid, indicating the presence of robust escape mutants which are not deterred by an immune system response to CPV types that are included in current vaccines. This was true not only for 2cΔ440, which causes a change in the primary sequence of the VP protein, but also for 2cΔ431, 2bΔ494Δ572, which do not contain amino acid changes in the regions studied. The significance of the 2bΔ494Δ572 codon changes has heretofore been unrecognized, and to our knowledge, there has up until now been no proposal to adjust the compositions of CPV vaccines and diagnostics to include or take into account these emerging variants, as is described herein. Further, 2cΔ440, 2bΔ431, and 2bΔ426Δ484Δ546 are novel mutants that have not been described previously.

Figure 7:
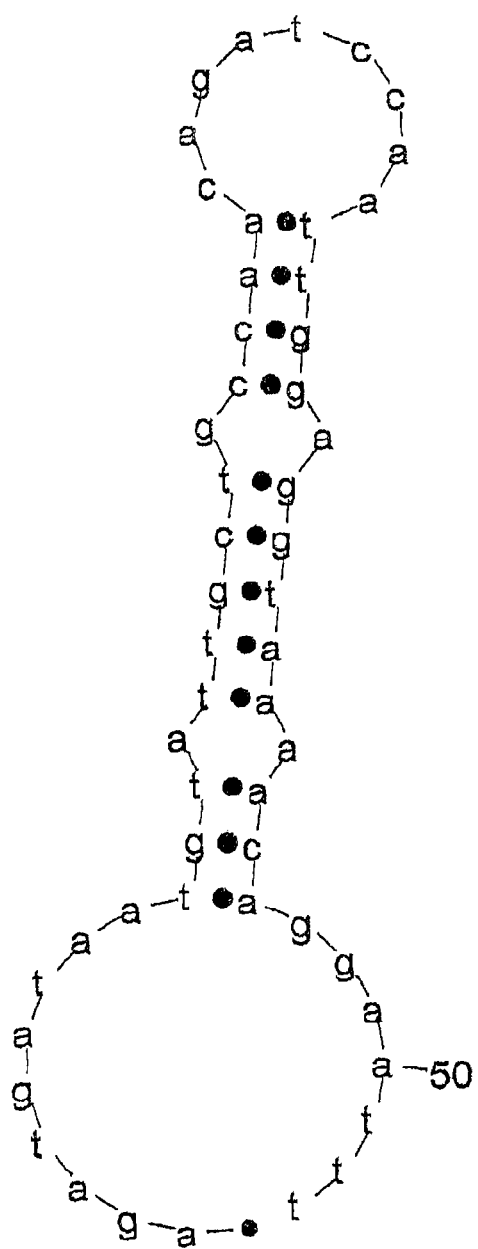
FIG. 7. Putative folded structure associated with the 2bΔ431 variant.
Figure 8:
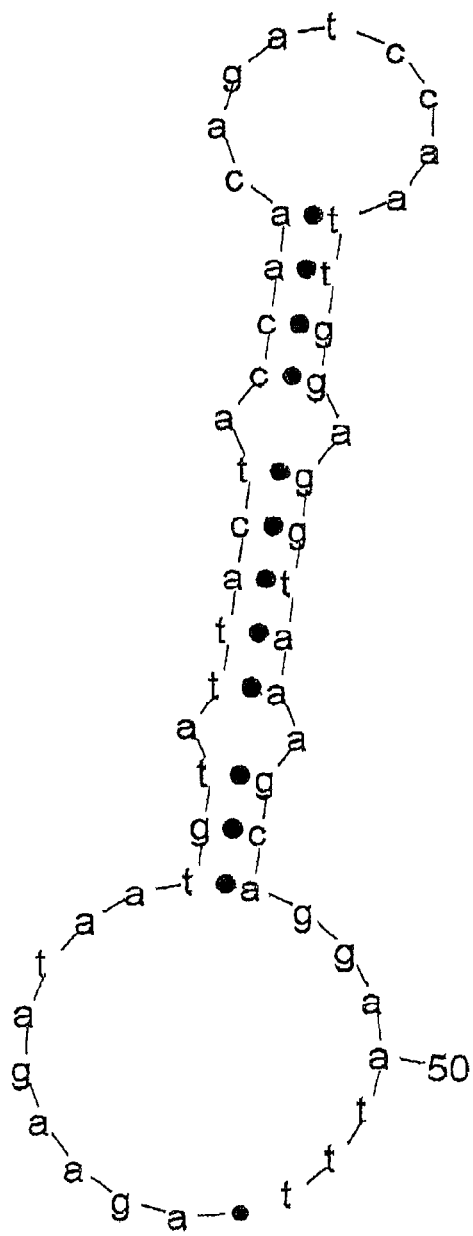
FIG. 8. Putative folded structure associated with the 2cΔ430Δ440 variant.

These variations appear to provide a survival advantage for the virus. Without being bound by theory, it is possible that the mutant sequences confer an advantage to the virion or to the DNA itself at some stage of the viral life cycle (e.g. protection against host nucleases; faster or more efficient transcription and/or translation, which could, for example, result in different patterns of protein folding; faster or more efficient packaging into the virion particle, etc.). For example, the mutant sequences may confer an advantage in terms of the thermodynamics of unfolding when DNA polymerase replicates the CPV DNA. FIGS. 6-8 depict the folded structures of the hypervariable region of CPV2c, CPV2bΔ431, and CPV2cΔ430Δ440, respectively, which are further described in Example 3.

In one embodiment of the invention, a successful, emerging CPV variant such as CPV2cΔ430Δ440 can be used as a challenge virus to check the value of commercial vaccine preparations under experimental conditions. Most older versions of CPV2a and CPV2b are not highly pathogenic to dogs, and the newer CPV2c has not been studied. Because of the lack of a highly virulent challenge model, up to now it has not been possible for vaccine companies to properly assess the ability of vaccine preparations to confer protection on vaccinated animals. The present invention thus also provides a method for doing so by exposing vaccinated animals to the highly virulent variant CPV2cΔ430Δ440, and assessing whether or not the vaccine protects against disease.

For each of the variants described herein, the invention encompasses vaccine preparations and diagnostics that include one or more of the variants, and methods of using the same. Preferably, such preparations and diagnostics include one or more of the novel variants 2cΔ440, 2bΔ431 and 2bΔ426Δ484Δ546. Such preparations and diagnostics may further include 2bΔ494Δ572 and/or American 2c, and/or other known CPV sequences, such as those that are already included in current vaccines. In addition, other newly isolated viruses with novel sequences, particularly with novel amino acid sequences, may or may not be suitable for inclusion in a new vaccine. In general, the decision to include a new field isolate is based on the ability of existing vaccines to elicit neutralizing responses to the field isolate in a vaccinated animal, and in part on the prevalence of the variant. If a new variant is ubiquitous, its antigenic significance should be determined. One measure of this is antigenic distance. The total antigenic distance of a particular CPV isolate can be determined by testing the isolate using a functional assay, such as serum neutralization titer and/or a hemagglutination assay and/or an indirect fluorescence antibody test. If, according to one or more assays, an isolate exhibits poor neutralization compared to viral variants already in the vaccine (i.e. if the level of neutralization of the new, heterologous isolate is more than 4-fold lower than the level of neutralization of variants already in the vaccine) then the development of a new vaccine which includes the new isolate may be warranted. For example, when a new CPV variant is isolated, the total antigenic distance can be calculated with a serum neutralization assay, and the results expressed as a neutralization titer. Neutralization titer is the inverse of the highest dilution of the serum from a vaccinated animal at which neutralization is complete evidenced by a lack of cytopathic effect (CPE) or presence of virus. If serum from dogs vaccinated with an existing CPV vaccine gives, for example a SN titer of 1:4000 with a homologous virus and a titer of 1:200 with a new heterologous CPV isolate, then the new isolate should likely be included in a CPV vaccine. In other words, if the current vaccine does not protect against a common, ubiquitous variant that is not in the current vaccine, then the variant may be with care included in a new vaccine preparation. If the isolate is localized in a small geographic area, then a custom or autogenous vaccine may be more suitable than a commercial vaccine designed for widespread use. The results should also be confirmed with challenge protection experiments. In challenge protection experiments, animals are vaccinated and then exposed to moderate doses (e.g. 10,000 TCID 50, i.e. median tissue culture infective dose) of a variant that is used as the challenge virus. If the vaccine provides protection against the variant, then the variant need not be included in vaccine compositions. However, if a vaccinated animal is not protected from the variant, the variant may be included in vaccine preparations. Further, during the vaccination process, not all strains or variants need to be included in the same injection. It may be preferable, for example, to administer a puppy shot that contains one variant at 3 weeks of age, a shot that contains a different variant at 7 weeks, and a shot that contains yet another variant at 10 weeks. This is in contrast to the current practice, in which the same variants are administered for all three puppy shots. This current procedure suffers from the drawback that existing immunity developed in response to an earlier vaccination can neutralize incoming CPV viruses delivered in later vaccinations, rendering later vaccinations of little or no use. Of note, it is well known that some viral pathogens can infect multiple species. In the case of CPV, feline and mink viruses have been known to also infect dogs. While the inclusion of such viruses in a canine CPV vaccine is not advisable, these feline and mink viruses should be included in challenge experiments of vaccinated animals.

In particular, variants 2bΔ431 and 2bΔ426Δ484Δ546 are useful in the preparation of vaccines suitable for forensic tracking and detection. As described above, current vaccines increasingly fail to protect vaccinated animals against emerging CPV, The owners of animals that are sickened after vaccination tend to blame the vaccine itself for causing disease. Because current diagnostic methods are inadequate to differentiate among vaccines strains and emerging strains, vaccine manufacturers have no practical defense against such accusations and frequently settle such claims by reimbursing the animals owners. This process is very costly for vaccine manufacturers. Also, the proximity of codon 431 to codon 426 and its location in the hypervariable region of the CPV genome also allows only limited sequencing to be done to verify the source of the causal CPV agent in a sick dog. This could be avoided by incorporating the 2bΔ431 and/or 2bΔ426Δ484Δ546 mutations into one or more of the vaccine strains that are used to formulate vaccines. 2bΔ431 and 2bΔ426Δ484Δ546 are extremely rare, e.g. 2bΔ431 represents only about 1.2% of the variants studied to date and 2bΔ426Δ484Δ546 has been detected in only one variant. Therefore, when tissue from a diseased animal that has been vaccinated with a 2bΔ431 or 2bΔ426Δ484Δ546 variant is tested for CPV, if any CPV strain other than 2bΔ431 or 2bΔ426Δ484Δ54 is detected, it can be confidently concluded that the vaccine did not cause the disease. Rather, the other detected strains were the likely culprit. Further, these mutations could be detected without extensive sequencing. This type of forensic investigation could provide significant savings to vaccine companies.

The invention provides vaccine preparations that comprise isolated nucleic acid sequences represented by SEQ ID NOS: 1, 2, 3, 4, 5 and 6 and/or proteins, polypeptides or peptides encoded by those sequences, and methods of their use. In addition, vaccines with certain variations of these sequences are also encompassed. While the sequences represent single-strand (ss) DNA, the invention also includes corresponding double-strand (ds) DNA, complementary DNA, and RNA of any form (e.g. mRNA, RNA/DNA hybrids, etc.) that is based on, derived from or that complements these sequences. Such sequences may be either sense or antisense sequences. Further, sequences which display at least about 50% homology, preferably about 60%, more preferably about 70, 80, or 90% homology, or even about 95, 96, 97, 98 or 99% or greater homology to SEQ ID NOS: 1, 2, 3, 4, 5 and 6 are also contemplated for use in the vaccines. Such sequences may differ, for example, by containing alternate codons that encode the same amino acid at one or more positions. In addition, portions of these sequences which encode antigenic regions of the CPV VP2 protein are also contemplated, as are sequences which display 70%, or even more preferably about 80, 90, or 95% or even greater identity (e.g. 96, 97, 98 or 99% identity) to such amino acid sequences. Such sequences may vary, for example, by containing conservative or non-conservative amino acid substitutions, or deletions (especially amino or carboxy terminal deletions), or various insertions, etc., so long as the resulting protein/peptide is antigenic as described herein. Such antigenic regions are preferably at least about 10 amino acids in length and encompass one or more of positions 426, 431, 440, 484, 494, 546, 555, and 572 of the VP protein. An antigenic region may, however, encompass an entire VP2 gene.

Further, nucleic acid sequences which hybridize to sequences disclosed herein (or to portions of those sequences) under stringent conditions (especially conditions of high stringency) are also contemplated. Stringent conditions refer to hybridization conditions which allow a nucleic acid sequence to hybridize to a particular sequence. In general, high stringent conditions refer to the hybridization conditions which allow a nucleic acid sequence of at least 50 nucleotides and preferably about 200 or more nucleotides to hybridize to a particular sequence at about 65° C. in a solution comprising about 1 M salt, preferably 6×SSC or any other solution having a comparable ionic strength, and washing at 65° C. in a solution comprising about 0.1 M salt, or less, preferably 0.2×SSC or any other solution having a comparable ionic strength. These conditions allow the detection of sequences having about 90% or more sequence identity. In general, lower stringent conditions refer to the hybridization conditions which allow a nucleic acid sequence of at least 50 nucleotides and preferably about 200 or more nucleotides to hybridize to a particular sequence at about 45° C. in a solution comprising about 1M salt, preferably 6×SSC or any other solution having a comparable ionic strength, and washing at room temperature in a solution comprising about 1M salt, preferably 6×SSC or any other solution having a comparable ionic strength. These conditions allow the detection of sequences having up to 50% sequence identity. The person skilled in the art will be able to modify these hybridization conditions in order to identify sequences varying in identity between 50% and 90%.

The invention also provides various types of recombinant vectors and/or expression systems that contain and express the nucleic acid sequences disclosed herein (or portions thereof that encode antigenic peptides and/or polypeptides). Examples of such vectors and expression systems include but are not limited to: various bacterial (e.g. *Escherichia coli*) or probiotic-based (e.g. *Lactobacillus*) expression vectors; adenoviral vectors, baculovirus, *Pichia*, and yeast expression systems, etc. Such recombinant vectors and expression systems may be utilized, for example, in vaccine preparations, or, alternatively, for other purposes such as for laboratory manipulation of the sequences, or for research or diagnostic purposes.

The invention provides immunogenic and/or vaccine compositions against canine parvovirus. The compositions comprise one or more of nucleic acid sequence SEQ ID NO: 1, 2, 3, 4, 5 and 6, or portions of those sequences which encode antigenic peptides or polypeptides (antigenic regions), e.g. portions of the sequence that include one or more of the codons for positions 426, 430, 431, 440, 484, 494, 546, 555, and 572. Preferably, at least sequences containing SEQ ID NO: 2 or SEQ ID NO: 4 or SEQ ID NO: 5 or SEQ ID NO: 6, or portions thereof which encode antigenic regions, will be included.

Those of skill in the art will recognize that vaccine compositions may also be varied according to projected use. In other words, the particular components (variants) included in the vaccine may be varied according to any of several parameters to create specially designed vaccine preparation. For example, vaccines can be designed to include only those variants that have been detected in a particular geographical location. For example, the 2a variant is no longer detected in the United States and thus vaccine manufacturers may choose not to include this variant in vaccine formulations to be used in the US. US vaccines might contain, for example, only CPV 2c and CPV 2b variants. In contrast, at present, 2a is the only CPV variant in Australia. Thus, a vaccine composition destined for use in Australia might include only the 2a variant. Recommended vaccines for Europe might include, for example, 2c and 2b variants, while a vaccine composition for Asia might include 2a and 2b. All such geographically tailored vaccines are encompassed by the present invention, and may be varied over time as the pattern of variant distribution changes. A further consideration with such geographically specific vaccines is that modified live virus vaccines contain high amounts of vaccine viral antigen. Thus, if a dog vaccinated with a variant is relocated to an area where that variant does not exist, it is preferable to quarantine the animal for at least about one month before release into the new environment. Otherwise, the variant may be released into the new location. For example, dogs vaccinated with a 2c variant should be quarantined prior to release in e.g. Australia. After the one month period, viral shedding should cease. Even though the shed virus is attenuated, its presence can confound attempts to monitor viral epidemiology, and could afford the opportunity for native viruses to recombine with the shed virus, resulting in introduction of the more virulent mutation into the local population.

In addition, vaccine compositions may be tailored for use in a particular host. For example, some breeds of dogs may be more susceptible to some variants than to others; or the life stage of the animal (e.g. puppy vs adult) may predispose an animal to susceptibility to one or more variants; or when hosts other than dogs are to be vaccinated (e.g. wild life, animals in zoos or on game reserves, etc.), the vaccine composition may be adjusted to take into account the susceptibility of the particular host animal that is to receive the vaccine. For example, in the development of a challenge model, Chihuahua and Labrador retriever breeds tend to be more susceptible to CPV. Thus, about 4 logs of the highly virulent CPV-2c variant should suffice to induce diarrhea and vomiting in a controlled setting. All such host-specific or host-selective vaccines are encompassed by the present invention.

In other embodiments, the vaccine composition may be adjusted according to the local environment of the vaccine recipient. For example, in commercial kennels housing more than 100 dogs, where the risk of contagious infection is high, vaccination with relatively expensive preparations containing variant 2bΔ431Δ494Δ572 and/or variant 2bΔ484Δ494Δ546Δ572 in combination with both the major and minor American CPV 2c variants may be preferred. However, in smaller kennels (e.g. with less than 25 dogs) or in homes with one or only a few dogs, where the risk of exposure is lower, vaccination with less expensive vaccines containing variants 2bΔ431Δ494Δ572 and/or 2bΔ484Δ494Δ546Δ572 together with only the major American 2c variant may suffice. When deciding which vaccine compositions to use, the risk of animals contracting the disease should be weighed against cost and the ability to molecularly monitor and assess the presence of CPV variants in the future.

In yet another facet, the invention provides a vaccine strategy for avoiding maternal antibody interference with vaccine immunity induction in puppies. Rather than use a single preparation of vaccine for adults and puppies, puppies can be vaccinated with a series of vaccines that differ antigenically. In other words, the initial puppy vaccine would contain variants that might differ from those that had been administered to the mother, and subsequent puppy booster shots would include yet other iterations of the vaccine. In this way, abroad spectrum of antibodies would be built up incrementally. The route of vaccination can be modified to overcome some vaccination limitations of, like shedding virus after parenteral immunization. For example, by using a supra-lingual vaccination route employing needle-less technology, immunity may be induced but shedding in the feces may be prevented.

Several methods of making vaccines suitable for vaccination against CPV are known in the art. See, for example, U.S. Pat. Nos. 4,193,990 and 4,193,991 to Appel et al., U.S. Pat. No. 4,303,645 to Carmichael et al., U.S. Pat. No. 4,971,793 to Wood et al.; U.S. Pat. No. 5,882,652 to Valdes et al., and U.S. Pat. No. 5,885,585 to Parrish et al., each of which offers variations of suitable vaccine-formulating strategies. The complete contents of each of these patents are hereby incorporated by reference. Generally, to manufacture a vaccine, a viral vector containing the described nucleic acid sequences (e.g. ssDNA naturally occurring within a virus, or ssDNA or other equivalent form genetically engineered into a non-native viral vector (e.g. dsDNA, ss or dsRNA, RNA-DNA hybrids, etc.) will be employed. Examples include CPV (or other) viruses that are "killed", inactivated or otherwise attenuated so as to not cause severe disease symptoms in the animal to which it is administered, together with a suitable physiological carrier. Preferably, no disease symptoms will occur as a result of administration. However, those of skill in the art will recognize that many effective vaccine compositions cause some discomfort or relatively minor distress upon or after administration. However, the benefits of being protected against full-blown disease far outweigh this possibility. As an alternative, a heterotypic virus that does not naturally infect or that does not normally cause disease in the animal being vaccinated may be utilized.

The attenuated virus may be a CPV that naturally contains the nucleic acid sequence(s), or the virus (CPV or other virus) may be recombinant in that the nucleic acid sequence is inserted into the virus by genetic engineering. In the case of recombinant vaccines, the nucleic acid sequences may be incorporated into viruses other than CPV to form heterotypic recombinant vaccines. Examples of such viruses include but are not limited to FPV, various herpesviruses, non-pathogenic "orphan viruses", enteric viruses such as enterovirus, etc. In a preferred embodiment, the virus is alive, attenuated (modified) high titer CPV, and the nucleic acid is ssDNA.

Preferably, such a preparation will also contain nucleic acid sequences encoding antigenic regions of other CPV variants, e.g. the 2, 2a, 2b and/or 2c variants, and any other CPV variants that may be subsequently identified and considered to be useful. However, given the wide distribution of vaccine compositions containing only the 2a and 2b variants, it may also be beneficial to produce vaccine compositions containing only one or more of the variants disclosed herein, for use in conjunction with and to complement the effects of the known 2a-2b vaccines. Further, such vaccines may be administered with vaccines against other disease causing entities, either as separate compositions, or together in a single composition.

The exact form of the vaccine may vary. In one embodiment, the vaccine is comprised of attenuated CPV viruses which contain nucleic acid sequences as disclosed herein. Preferably the vaccine is multivalent and also includes attenuated CPV 2, 2a, 2b, and/or 2c type viruses. Alternatively, a single virus may be genetically engineered to contain nucleic acids encoding proteins (e.g. VP2 proteins, or antigenic portions thereof) from two or more variant types, i.e. recombinant chimeric CPVs having genomic regions from two or more regions of VP2 can be constructed by recombinant technology by exchanging DNA regions from two or more CPVs, as is known by those of skill in the art.

Other forms of the vaccine are also contemplated. For example, "empty" virion particle vaccines (without nucleic acid) are also contemplated, as are vaccines comprising antigenic virion or other CPV proteins that are not assembled into a capsid. In these cases, the proteins in the vaccine preparation are encoded by one or more of SEQ ID NO: 2, SEQ ID NO:4 and SEQ ID NO: 6, or alternatively, shorter antigenic regions are encoded by portions of SEQ ID NO:2 and/or SEQ ID NO:4 and/or SEQ ID NO: 5 and/or SEEQ ID NO: 6. Proteins encoded by SEQ ID NO: 1 and/or SEQ ID NO: 3, and/or antigenic regions encoded by portions of SEQ ID NO: 1 and/or SEQ ID NO: 3 may also be included.

Other suitable vaccine components, e.g. pharmacologically acceptable carriers, are well-known to those of skill in the art, as is the preparation of such compositions for use as vaccines. Typically, such compositions are prepared either as liquid solutions or suspensions, however solid forms such as tablets, pills, powders and the like are also contemplated. Solid forms suitable for solution in, or suspension in, liquids prior to administration may also be prepared. The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of the translatable nucleic acid in the formulations may vary. However, in general, the amount will be from about 1-99%. The compositions may further comprise an adjuvant, suitable examples of which include but are not limited to Seppic, Quil A, Alhydrogel, etc.

The immunogenic/vaccine preparations of the present invention may be administered by any of many suitable means which are well known to those of skill in the art, including but not limited to by injection, orally, intranasally, by ingestion of a food product containing the antigen, etc. However, in preferred a embodiment, the mode of administration is by injection. In addition, the compositions may be administered alone or in combination with other medicaments or immunogenic compositions, e.g. as part of a multicomponent vaccine. Further, administration may be a single event, or multiple booster doses may be administered at various timed intervals to augment the immune response. In addition, administration may be prophylactic, i.e. before exposure to the virus has occurred, or is suspected to have occurred, or after the fact, i.e. after a known or suspected exposure, or therapeutically, e.g. after the occurrence of disease symptoms associated with viral infection.

Upon administration of the preparation, the nucleic acid sequences of the invention are expressed within the host animal to whom the vaccine has been administered, and the host animal mounts an immune response to the antigenic proteins (or portions thereof) encoded by the nucleic acid. Preferably, the immune response that is elicited is a protective immune response. In some embodiments, the attenuated virus retains the ability to replicate within the host, although this is not strictly necessary.

The invention provides methods of preventing the symptoms of CPV infection in a mammal in need thereof. Generally, the CPV vaccines are administered to provide active immunity in puppies and/or adult dogs. The method involves administering to the mammal an immunogenic and/or vaccine composition comprising a nucleic acid that includes the sequence represented by at least one of SEQ ID NO: 2 and SEQ ID NO: 4, SEQ ID NO: 5, or SEQ ID NO: 6, or portions thereof which encode antigenic regions of VP2, and preferably comprising sequences represented by one or more of SEQ ID NO: 1, SEQ ID NO: 2, SEQ ID NO: 3, SEQ ID NO: 4, SEQ ID NO: 5 and SEQ ID NO: 6, or portions thereof which encode antigenic regions of VP2. In a preferred embodiment, the preparation also includes nucleic acids encoding other clinically relevant CPV variants, preferably the 2a and 2b variants, and, optionally, the original CPV2. Administration of the composition results in the elicitation of an immune response by the recipient. Preferably, the immune response is protective against future exposure to CPV, and either eliminates disease symptoms entirely, or ameliorates disease symptoms to a milder level than would be experienced without vaccination.

In a preferred embodiment of the invention, the animals that are vaccinated using the vaccines of the invention are domestic dogs, including both adult dogs and puppies. However, the vaccination of other potential CPV hosts is also contemplated. Other potential hosts include other canids such as wild canids (e.g. wolves, wild dog species, etc.), cats (including domestic cats and kittens, and larger species of cats, whether domesticated or wild), mink, red panda, foxes, lion and tigers, etc. While the vaccines will of course be used in domestic animals, wild or partially domesticated animals may also benefit from such vaccination, e.g. animals in zoos or protected areas, parks, in research facilities, etc. Any animal that can host the CPV and CPV variants, whether or not the virus causes disease symptoms in the host, may benefit by being vaccinated by the vaccine preparations provided herein. Vaccination of animals that are asymptomatic upon infection by the virus (i.e. silent carriers) would be beneficial in order to curtail the spread of the virus to more susceptible populations.

The invention also provides antibodies that bind specifically or selectively to antigenic determinants or antigenic regions of proteins of the type 2bΔ494Δ572, 2bΔ426Δ484Δ546, 2bΔ431, 2cΔ440 and or American 2c variant CPVs. Such differential antibodies may be polyclonal or monoclonal, although monoclonal antibodies are generally preferred. Monoclonal antibodies will be prepared by injecting the variants (either in protein form, or nucleic acids ancoding the proteins) in mice. After 3 boosters, the spleens will be harvested and fused with myeloma cells. The monoclonal antibodies producing clones will be screened by ELISA, HA-HI, and indirect fluorescent antibody test. The clones that react with 2bΔ494Δ572, 2bΔ426Δ484Δ546, 2bΔ431, 2cΔ440 and/or American 2c genotypes will be saved for development of CPV diagnostic assays. Polyclonal antibodies may be prepared by injecting one or more peptides that span the amino acid codons that are preferred antigenic targets of the 2bΔ494Δ572, 2bΔ426Δ484Δ546, 2bΔ431, 2cΔ440 and/or American 2c variants e.g. into rabbits.

The invention also provides diagnostic kits for the detection of the CPV variants described herein, and, optionally, of other CPV variants as well (e.g. CPV2, 2a and 2b). Such kits include oligonucleotide primers specific for amplifying (e.g. by polymerase chain reaction) the nucleic acid sequences disclosed herein. Alternatively, such kits may include antibodies (e.g. monoclonal or polyclonal) that bind selectively or specifically to unique antigenic determinants displayed by the variants, and, optionally, other CPV variants as well (e.g. CPV2, 2a and 2b).

In a further aspect of the invention, a new method for culturing CPV in vitro is provided. The method involves culturing the virus in a mixed cell culture of 1) cells that are known to be susceptible to infection by CPV, and 2) Vero cells, in a suitable medium. In a preferred embodiment, the cells that are susceptible to infection by CPV are CRFK cells. However, other types of such cells may also be used, including but not limited to: A72 canine fibroma-derived cells; cells derived from CRFK cells such as Nordisk Laboratory feline kidney (NLFK) cells; feline tongue cells such as Fe3Tg cells; feline lung cells such as AK-D cells; feline lymphoma cell lines such as 3201; canine T-cell lines such as CT 45-S; canine thymus epithelial cells lines such as Cf2Th, etc. Moreover, a variety of feline and canine cell lines, as well as instructions for culturing them, may be obtained from the American Type Culture Collection in Manassas, Va.

These cell lines can be propagated, together with Vero cells, in a variety of media which are known to those of skill in the art. For example, CT 45-S cells can be cultured in RPMI 1640 media; AK-D, Fe2lu and Cf2Ths cells may be cultured in Dulbecco's minimal essential media (MEM) with 10% fetal bovine serum (FBS); for 3201, NLFK, CRFL, A72 and Fc3 Tg cells, McCoy's 5A and Leibowitz L15 with 5% FCS and be used. Typically, the cell lines are incubated together for 4-5 days at 37° C.

EXAMPLES

Introduction

Canine parvovirus (CPV) infection is the most serious and prevalent disease of dogs, and is the most common cause of diarrhea in puppies. Although vaccines against CPV are available and widely used, several recent outbreaks of CPV in vaccinated dogs have occurred. For example, kennel owners in South Central United States have observed high rates of puppy mortality due to CPV infection in spite of vaccination.

CPV is a single-stranded DNA virus that has a high rate of mutation and the ability to change its host range and tropism. Commercial vaccines that are currently available typically contain only the CPV2, CPV2a, and CPV2b variants. During our analysis of samples from CPV vaccinated dogs with overt symptoms of parvovirus infection, we observed functional changes in CPV detection by current CPV diagnostic tests and failure of the current kits to detect the field virus, indicating possible evolution of CPV beyond the 2a and 2b subtypes. Further investigations resulted in the identification of two variants of CPV, namely 2bΔ494Δ572 and American 2c. The isolates are associated with enhanced virulence and broader tissue tropism than is observed with heretofore cultured CPV isolates. In addition, it appears that the new CPV isolates cause yellow mucous diarrhea instead of hemorrhagic diarrhea caused by CPV-2 genotypes in the past. Consistent with other reports, the 2bΔ494Δ572 variant has two codon changes. The American 2c variant has been previously detected in Italy, Spain and Vietnam, but has not been previously detected in the United States.

Materials and Methods

Fecal Samples were Received by the Oklahoma Animal Disease Diagnostic

Laboratory by Federal Express over ice packs (about 4-5° C.). A minimum of 2-5 grams of feces or 2-5 ml of liquid diarrhea stools were received. The fecal samples are generally tested the same day by CPV Enzyme Linked Immunosorbent Assay (ELISA)(s) that are commercially available. We receive intestinal loops (about 2-3 pieces) from different regions of the gut for fluorescent antibody test (FAT) or immunohistochemistry (IHC). Sometimes, we received pieces of the tongue for FAT or IHC or polymerase chain reaction (PCR) for CPV examination. These specimens are received cool over ice packs by FedExp. Many CPV cases have a history of testing negative for CPV by field diagnostic kits (Assure, Synbiotics, CA; or IDEXX, Bar Harbor, Me.).

Histopathology was performed on the intestines of puppies and adult dogs with a history compatible with CPV. The history included bloody or mucous diarrhea, and death. Fresh and formalin-fixed intestinal tissues were examined for lesions compatible with CPV: crypt dilatation and necrosis, and loss of intestinal villi.

Fluorescent antibody (FAT) test was used to screen the intestines for CPV antigen. The intestinal sections 6-8 micrometers in thickness were fixed with acetone and air dried. Anti CPV conjugate labeled with FITC was added and sections were incubated for 30 min at 37° C. After washes, the sections were counterstained with trypan blue. The sections were examined by fluorescent microscopy: CPV positive cells stain apple green and CPV negative cells stain brick red with a FAT test.

Formalin-fixed sections submitted for histopathology were examined by immuno-histochemistry for CPV antigen.

PCR followed by sequencing were carried out on fecal samples and scrapings of the CPV positive or suspected intestinal samples, as described by Desario et al., 2005. A portion of the viral protein gene was amplified by PCR. The amplified PCR product was detected by agarose gel electrophoresis and eluted from the gel for sequencing.

Sequences were subjected to analysis by the BLAST program that compares the results with a vast collection of sequences that have been deposited in the GenBank. All the sequences were identified as similar to canine parvovirus.

Example 1

Failure of Current CPV Diagnostic Tests

Fecal samples were analyzed as described above, and all samples were positive using the standard criteria of: characteristic lesions as determined by histopathology, fluorescent antibody test results, and immuno-histochemistry results. Nevertheless, upon testing of the same samples using commercial diagnostic tests, the results showed that the tests were unreliable for CPV field diagnosis of these samples, failing to detect 33-50% of CPV positive cases.

Most of these CPV isolates were obtained from kennels that are currently using commercial CPV vaccines according to the vaccine label but still experiencing CPV outbreaks and mortality. This lack of protection is likely due to antigenic variation in the newly emerging CPV isolates. This epidemiological field observation over many CPV cases (n~500) signals the need to incorporate these new CPV variants into commercial CPV vaccines.

Example 2

Sequencing of CPV Isolates: Identification of 2bΔ494Δ572 Variant and American CPV2c Isolate The failure of vaccines and diagnostic kits is generally considered to be epidemiological evidence of viral evolution. Therefore, the presence of new CPV variants in the samples being studied was suspected. To confirm this, PCR-sequencing of a portion of the viral protein VP2 was carried out for viruses isolated from the fecal samples, and the results were compared to known VP2 sequences using computer software programs and/or manual alignment.

The results confirmed the presence of two newly emerging CPV types in the samples: 1) a variant of 2b which was denominated 2bΔ494Δ572; and 2) American 2c, which had not been previously reported in the United States. The DNA sequences encoding portions of the VP2 proteins of the two variants are presented in FIG. 1 (2bΔ494Δ572, SEQ ID NO: 1) and FIG. 3 (American 2c, SEQ ID NO: 3). A comparison of these sequences to a known CPV 2 reference sequence revealed that, in 2bΔ494Δ572, a change in codons 494 and 572 had taken place. The usual CPV 2 codon at 494 is TGT but in 2bΔ494Δ572 codon 494 is TGC. Similarly, the usual codon at position 572 in CPV2 isolates is GTA but in 2bΔ494Δ572 this codon is GTC. These changes do not result in changes in the amino acid sequence of the VP2 protein. However, it is likely that the changes confer advantages to the 2bΔ494Δ572 variant in one or more phases of its life cycle, e.g. in replication, transcription or translational efficiency. Significantly, the presence of the American 2c variant in the samples is the first report of this CPV variant in the United States and is likely a harbinger of its emergence as a dominant variant. About 50% of the cases of vaccine failure were due to the presence of the CPV2bΔ494Δ572 and 50% were attributable to CPV2c or CPV2cΔ430Δ440.

These findings demonstrate the emergence of 2bΔ494Δ572 (SEQ ID NO: 1) and American 2c (SEQ ID NO: 3) as dominant CPV variants, and signal the need to incorporate these variants into CPV vaccine preparations.

Other variants were identified in a similar manner. In particular, the novel variant 2bΔ426Δ484Δ546 (SEQ ID NO: 6), which is highly cytopathic, has also been identified in this manner.

Example 3

Determination of Variant Secondary Structure and Associated Energy

The virulence of viral pathogens is known to be associated with secondary structural elements in the viral genome (Pellerin et al., 1994. Virology 203: 260-268). The folding patterns of hypervariable regions of variants 2c, 2bΔ431 and 2cΔ430Δ440 were assessed using the "mfold" DNA folding program at the web site located at mfold.burnet.edu.au on the World Wide Web. The results are shown in FIGS. 6-8, which depict the folding patterns and associated energy levels for each variant. As can be seen, the secondary structure of the region is maintained and the energy levels for unfolding can change.

Example 4

Development and Testing of a New Multivalent Vaccine Against CPV

A new multivalent vaccine that is protective against newly emerging CPV variants is developed. The vaccine includes one or more attenuated CPV viruses of types CPV2b, 2bΔ494Δ572 (SEQ ID NO 1), 2bΔ431 (SEQ ID NO 2), 2bΔ426Δ484Δ546 (SEQ ID NO 6), American 2c (SEQ ID NO 3), 2cΔ440 (SEQ ID NO 4), and, optionally, CPV2. In other words, in this novel vaccine, CPV2b is replaced by 2bΔ494Δ572 and/or 2bΔ426Δ484Δ546, the variants that have newly been discovered to be emerging as the dominant genotype. The presence of CPV2, which appears to no longer be a threat, is optional.

Animals vaccinated with the multivalent vaccine are protected against developing symptoms of parvovirus infection by the variants used to prepare the vaccine.

Example 5

Novel Mixed Cell Culture Methods for CPV Propagation

CPV is typically grown in a cell cultures containing only a single type of cell such as the Crandall feline kidney (CRFK) cell line.

An improved method of culturing CPV has been developed. According to the new method, CPV is cultivated in an equal mixture of CRFK and Vero cells in minimum essential medium (MEM). Both the cell lines were plated and samples were inoculated one hour after plating. At this stage the cells were attached but still in the early stages of cell division. The new cell culture method produced detectable cytopathic effects more rapidly than when the CPV was cultivated with CRFK cells alone. Moreover, high titers of CPV production were maintained in the mixed cell culture for 3 serial passages.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein. All United States patents, patent applications, and other references cited herein are hereby incorporated by reference.

REFERENCES

Buonavoglia, Canio, V. Martella, A. Pratelli, M. Tempesta, A. Cavalli, D. Buonavoglia, G. Bozzo, G. Elia, N. Decaro and L. Carmichael, *J. Gen. Virol.* (2001) 82, 3021-3025.

Decaro, Nicola, V. Martella, G. Elia, C. Desario, M. Compolo, E. Lorusso, M. L. Colaianni, A. Lorusso, and C. Buonavoglia, *Vet. Micro.* 121 (2007) 39-44.

Desario, Constantina, N. Decaro, M. Campolo, A. Cavalli, F. Cirone, G. Elia, V. Martella, E. Lorusso, M. Camero and C. Buonavoglia. *J. Virol. Methods* 126 (2005) 179-185.

Nakamura, Kazuya, M. Sakamoto, Y. Ikeda, E., Sato, K. Kawakami, T. Miyazawa, Y. Tohya, E. Takahashi, E. Mikami, T. Mikami and M. Mochizuki. *Clin. Diag. Lab. Immuno.* (2001) 663-668.

Nakamura M., Tohya, Y., Miyazawa, T., Mochizuki, M., Phung, H. T., Nguyen, N. H., Huynh, L. M., Nguyen, L. T., P. N. Nguyen, P. N., Nguyen, P. V., Akashi, H. (2004) *Arch. Virol.* 149, 2261-2269.

Parrish, Colin R. And and Yoshihiro Kawaoka, *Annu. Rev. Microbiol.* (2005) 59, 553-86.

Truyen, Uwe. *Veterinary Microbiology* (2006) 117, 9-13.

We claim:

1. A recombinant vector that contains and expresses a nucleic acid sequence encoding a canine parvovirus VP-2 protein, wherein said nucleic acid sequence is at least 99% homologous to SEQ ID NO: 6, wherein: nucleotides 1-3 of said nucleic acid sequence are GAC to encode Asp at position 426 of said VP-2 protein, nucleotides 175-177 of said nucleic acid sequence are GTG to encode Val at position 484 of said VP-2 protein, and nucleotides 361-363 of said nucleic acid sequence are AAC to encode Asn at position 546 of said VP-2 protein.

2. The recombinant vector of claim 1, wherein said nucleic acid sequence encoding a canine parvovirus VP-2 protein is SEQ ID NO: 6.

3. The recombinant vector of claim 1, wherein said recombinant vector further comprises one or more nucleic acid sequences encoding a VP-2 protein selected from the group consisting of: SEQ ID NO: 1; a portion of SEQ ID NO: 1 that encodes an antigenic region of said VP-2 protein; SEQ ID NO:2; a sequence that is at least 95% homologous to SEQ ID NO: 2, wherein nucleotides 16-18 are CTG to encode Leu at position 431 of said VP-2 protein; SEQ ID NO: 3; a portion of SEQ ID NO: 3 that encodes an antigenic region of said VP-2 protein; SEQ ID NO: 4; a sequence that is at least 95% homologous to SEQ ID NO: 4 and wherein nucleotides 43-45 are GCA to encode Ala at position 440 of said VP-2 protein; SEQ ID NO: 5, a portion of SEQ ID NO: 5 that encodes an antigenic region of said VP-2 protein; a nucleic acid sequence encoding a CP-V2 VP-2 protein, a nucleic acid sequence encoding a CP-V2a VP-2 protein, a nucleic acid sequence encoding a CP-V2b VP-2 protein, a nucleic acid sequence encoding a CP-V2c VP-2 protein.

4. The recombinant vector of claim 3, wherein said recombinant vector is selected from the group consisting of bacterial vectors, probiotic-based expression vectors, viral vectors, and yeast expression vectors.

5. The recombinant vector of claim 3, wherein said bacterial vector is an *Escherichia coli* vector.

6. The recombinant vector of claim 3, wherein said probiotic-based expression vector is a *Lactobacillus* vector.

7. The recombinant vector of claim 3, wherein said viral vectors are adenoviral vectors or baculovirus vectors.

8. The recombinant vector of claim 3, wherein said yeast expression vectors is a *Pichia* vector.

9. An immunogenic composition comprising a recombinant vector that contains and expresses a nucleic acid sequence encoding a canine parvovirus VP-2 protein, wherein said nucleic acid sequence is at least 99% homologous to SEQ ID NO: 6, wherein: nucleotides 1-3 of said nucleic acid sequence are GAC to encode Asp at position 426 of said VP-2 protein, nucleotides 175-177 of said nucleic acid sequence are GTG to encode Val at position 484 of said VP-2 protein, and nucleotides 361-363 of said nucleic acid sequence are AAC to encode Asn at position 546 of said VP-2 protein.

10. The immunogenic composition of claim 9, wherein said nucleic acid sequence encoding a canine parvovirus VP-2 protein is SEQ ID NO: 6.

11. The immunogenic composition of claim 9, wherein said recombinant vector further comprises one or more nucleic acid sequences selected from the group consisting of: SEQ ID NO: 1; a portion of SEQ ID NO: 1 that encodes an antigenic region of said VP-2 protein; SEQ ID NO:2; a sequence that is at least 95% homologous to SEQ ID NO: 2, wherein nucleotides 16-18 are CTG to encode Leu at position 431 of said VP-2 protein; SEQ ID NO: 3; a portion of SEQ ID NO: 3 that encodes an antigenic region of said VP-2 protein; SEQ ID NO: 4; a sequence that is at least 95% homologous to SEQ ID NO: 4 and wherein nucleotides 43-45 are GCA to encode Ala at position 440 of said VP-2 protein; SEQ ID NO: 5, a portion of SEQ ID NO: 5 that encodes an antigenic region of said VP-2 protein; a nucleic acid sequence encoding a CP-V2 VP-2 protein, a nucleic acid sequence encoding a CP-V2a VP-2 protein, a nucleic acid sequence encoding a CP-V2b VP-2 protein, a nucleic acid sequence encoding a CP-V2c VP-2 protein.

12. The immunogenic composition of claim 9, wherein said immunogenic composition further comprises one or more recombinant vectors that contain and express one or more nucleic acid sequences selected from the group consisting of: SEQ ID NO: 1; a portion of SEQ ID NO: 1 that encodes an antigenic region of said VP-2 protein; SEQ ID NO:2; a sequence that is at least 95% homologous to SEQ ID NO: 2, wherein nucleotides 16-18 are CTG to encode Leu at position 431 of said VP-2 protein; SEQ ID NO: 3; a portion of SEQ ID NO: 3 that encodes an antigenic region of said VP-2 protein; SEQ ID NO: 4; a sequence that is at least 95% homologous to SEQ ID NO: 4 and wherein nucleotides 43-45 are GCA to encode Ala at position 440 of said VP-2 protein; SEQ ID NO: 5, a portion of SEQ ID NO: 5 that encodes an antigenic region of said VP-2 protein; a nucleic acid sequence encoding a CP-V2 VP-2 protein, a nucleic acid sequence encoding a CP-V2a VP-2 protein, a nucleic acid sequence encoding a CP-V2b VP-2 protein, a nucleic acid sequence encoding a CP-V2c VP-2 protein.

13. The immunogenic composition of claim 9, wherein said recombinant vector is selected from the group consisting of bacterial vectors, probiotic-based expression vectors, adenoviral vectors, baculovirus vectors, and yeast expression vectors.

14. The immunogenic composition of claim 13, wherein said bacterial vector is an *Escherichia coli* vector.

15. The immunogenic composition of claim 13, wherein said probiotic-based expression vector is a *Lactobacillus* vector.

16. The immunogenic composition of claim 13, wherein said viral vectors are adenoviral vectors or baculovirus vectors.

17. The immunogenic composition of claim 13, wherein said yeast expression vector is a *Pichia* vector.

* * * * *

SEQUENCE LISTING

```
<160> NUMBER OF SEQ ID NOS: 6

<210> SEQ ID NO 1
<211> LENGTH: 441
<212> TYPE: DNA
<213> ORGANISM: Canine parvovirus

<400> SEQUENCE: 1
gatgataatg tattgctacc aacagatcca attggaggta aaacaggaat taactatact      60
aatatattta atacttatgg tcctttaact gcattaaata atgtaccacc agtttatcca     120
aatggtcaaa tttgggataa agaatttgat actgacttaa aaccaagact tcatgtaaat     180
gcaccatttg tttgtcaaaa taattgccct ggtcaattat ttgtaaaagt tgcgcctaat     240
ttaacaaatg aatatgatcc tgatgcatct gctaatatgt caagaattgt aacttactca     300 gattttggt ggaaaggtaa attagtattt aaagctaaac taagagcctc tcatacttgg     360
aatccaattc aacaaatgag tattaatgta gataaccaat ttaactatgt accaagtaat     420
attggaggta tgaaaattgt c                                              441

<210> SEQ ID NO 2
<211> LENGTH: 441
<212> TYPE: DNA
<213> ORGANISM: Canine parvovirus

<400> SEQUENCE: 2
gatgataatg tattgctgcc aacagatcca attggaggta aaacaggaat taactatact      60
aatatattta atacttatgg tcctttaact gcattaaata atgtaccacc agtttatcca     120
aatggtcaaa tttgggataa agaatttgat actgacttaa aaccaagact tcatgtaaat     180
gcaccatttg tttgtcaaaa taattgccct ggtcaattat ttgtaaaagt tgcgcctaat     240
ttaacaaatg aatatgatcc tgatgcatct gctaatatgt caagaattgt aacttactca     300 gattttggt ggaaaggtaa attagtattt aaagctaaac taagagcctc tcatacttgg     360
aatccaattc aacaaatgag tattaatgta gataaccaat ttaactatgt accaagtaat     420
attggaggta tgaaaattgt c                                              441

<210> SEQ ID NO 3
<211> LENGTH: 441
<212> TYPE: DNA
<213> ORGANISM: Canine parvovirus

<400> SEQUENCE: 3
gaagataatg tattgctacc aacagatcca attggaggta aaacaggaat taactatact      60
```

| | |
|---|---|
| aatatattta atacttatgg tcctttaact gcattaaata atgtaccacc agtttatcca | 120 |
| aatggtcaaa tttgggataa agaatttgat actgacttaa aaccaagact tcatgtaaat | 180 |
| gcaccatttg tttgtcaaaa taattgtcct ggtcaattat ttgtaaaagt tgcgcctaat | 240 |
| ttaacaaatg aatatgatcc tgatgcatct gctaatatgt caagaattgt aacttactca | 300 |
| gattttggt ggaaaggtaa attagtattt aaagctaaac taagagcctc tcatacttgg | 360 |
| aatccaattc aacaaatgag tattaatgta gataaccaat ttaactatgt accaagtaat | 420 |
| attggaggta tgaaaattgt a | 441 |

<210> SEQ ID NO 4
<211> LENGTH: 441
<212> TYPE: DNA
<213> ORGANISM: Canine parvovirus

<400> SEQUENCE: 4

| | |
|---|---|
| gaagataatg tattgctacc aacagatcca attggaggta aagcaggaat taactatact | 60 |
| aatatattta atacttatgg tcctttaact gcattaaata atgtaccacc agtttatcca | 120 |
| aatggtcaaa tttgggataa agaatttgat actgacttaa aaccaagact tcatgtaaat | 180 |
| gcaccatttg tttgtcaaaa taattgtcct ggtcaattat ttgtaaaagt tgcgcctaat | 240 |
| ttaacaaatg aatatgatcc tgatgcatct gctaatatgt caagaattgt aacttactca | 300 |
| gattttggt ggaaaggtaa attagtattt aaagctaaac taagagcctc tcatacttgg | 360 |
| aatccaattc aacaaatgag tattaatgta gataaccaat ttaactatgt accaagtaat | 420 |
| attggaggta tgaaaattgt a | 441 |

<210> SEQ ID NO 5
<211> LENGTH: 441
<212> TYPE: DNA
<213> ORGANISM: Canine parvovirus

<400> SEQUENCE: 5

| | |
|---|---|
| gaagataatg tattactacc aacagatcca attggaggta aagcaggaat taactatact | 60 |
| aatatattta atacttatgg tcctttaact gcattaaata atgtaccacc agtttatcca | 120 |
| aatggtcaaa tttgggataa agaatttgat actgacttaa aaccaagact tcatgtaaat | 180 |
| gcaccatttg tttgtcaaaa taattgtcct ggtcaattat ttgtaaaagt tgcgcctaat | 240 |
| ttaacaaatg aatatgatcc tgatgcatct gctaatatgt caagaattgt aacttactca | 300 |
| gattttggt ggaaaggtaa attagtattt aaagctaaac taagagcctc tcatacttgg | 360 |
| aatccaattc aacaaatgag tattaatgta gataaccaat ttaactatgt accaagtaat | 420 |
| attggaggta tgaaaattgt a | 441 |

<210> SEQ ID NO 6
<211> LENGTH: 441
<212> TYPE: DNA
<213> ORGANISM: Canine parvovirus

<400> SEQUENCE: 6

| | |
|---|---|
| gacgataatg tattgctacc aacagatcca attggaggta aaacaggaat taactatact | 60 |
| aatatattta atacttatgg tcctttaact gcattaaata atgtaccacc agtttatcca | 120 |
| aatggtcaaa tttgggataa agaatttgat actgacttaa aaccaagact tcatgtgaat | 180 |
| gcaccatttg tttgtcaaaa taattgccct ggtcaattat ttgtaaaagt tgcgcctaat | 240 |
| ttaacaaatg aatatgatcc tgatgcatct gctaatatgt caagaattgt aacttactca | 300 |

```
gatttttggt ggaaaggtaa attagtattt aaagctaaac taagagcctc tcatacttgg    360
aacccaattc aacaaatgag tattaatgta gataaccaat ttaactatgt accaagtaat    420
attggaggta tgaaaattgt c                                              441
```